US00PP36692P2

(12) United States Plant Patent
Miller

(10) Patent No.: US PP36,692 P2
(45) Date of Patent: May 20, 2025

(54) ***CLEMATIS* PLANT NAMED 'DP136'**

(50) Latin Name: ***Clematis* hybrid**
Varietal Denomination: DP136

(71) Applicant: Early Morning LLC, Greendale, IN (US)

(72) Inventor: Mike Miller, Wilmette, IL (US)

(73) Assignee: EARLY MORNING LLC, Greendale, IN (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 18/511,452

(22) Filed: Nov. 16, 2023

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02
See application file for complete search history.

(56) References Cited

PUBLICATIONS https://deal.town/spring-hill-nurseries/clematis-are-in-vogue-especially-these-FK35U5RTD; Dec. 11, 2022; 3 pages.*
*Clematis* Strawberry Shortcake—Shop *Clematis* | Spring Hill Nurseries—Spring Hill Nursery ; Oct. 2, 2024; 7 pages.*

* cited by examiner

*Primary Examiner* — Kent L Bell
(74) *Attorney, Agent, or Firm* — Weatherly IP Solutions, LLC; James M. Weatherly

(57) ABSTRACT

A new *Clematis* plant, particularly distinguished by abundant purple and pink flowers on old growth; double flowers produced on new growth; and compact growth with short internodes, is disclosed.

1 Drawing Sheet

Genus and species: *Clematis* hybrid.
Variety denomination: 'DP136'.

BACKGROUND OF THE NEW PLANT

The present invention relates to a new and distinct variety of *Clematis*, hereinafter referred to by the variety name 'DP136'. 'DP136' arose from an open pollination in 2006 in Evanston, Illinois, between an unnamed female *Clematis* seedling (unpatented) and an unknown male *Clematis* line. Seeds from the pollination were collected, sown and germinated in 2007 in Evanston, Illinois.

A seedling was selected in 2007 and named 'DP136'. 'DP136' was first asexually propagated in Evanston, Illinois, by softwood cuttings. 'DP136' was found to reproduce true to type in successive generations of asexual propagation via softwood cuttings.

SUMMARY

The following are the most outstanding and distinguishing characteristics of this new variety when grown under normal horticultural practices in Tipp City, Ohio.

1. Abundant purple and pink flowers on old growth;
2. Double flowers are produced on new growth; and
3. Compact growth and short internodes.

DESCRIPTION OF THE PHOTOGRAPH

This new *Clematis* plant is illustrated by the accompanying photograph of a two-year-old plant in Tipp City, Ohio in July of 2023. The photograph shows the plant's overall plant habit, leaves and flowers. The colors shown are as true as can be reasonably obtained by conventional photographic procedures.

DESCRIPTION OF THE NEW VARIETY

The following detailed descriptions are set for the distinctive characteristics of 'DP136'. Measurements were taken from a three-year-old plant grown in an open field on a fence as a trellis in Tipp City, Ohio in July 2023. Color references are to The R.H.S. Colour Chart of The Royal Horticultural Society of London (R.H.S.) 2001.

Classification:
- *Family*.—Ranunuculaceae.
- *Botanical*.—*Clematis* hybrid.
- *Designation*.—'DP136'.

Parents:
- *Female*.—Unnamed female *Clematis* seedling (unpatented).
- *Male*.—Unknown.

Plant:
- *Type*.—Climbing.
- *Vigor*.—Moderate.
- *Typical plant height*.—120 cm to 150 cm.
- *Typical plant spread*.—75 cm to 105 cm.
- *Time to root initiation*.—21 days.
- *Time to produce a rooted plant*.—90 to 120 days.
- *Root description and color*.—Fleshy, RHS 164C.
- *Young shoot, presence of pubescence*.—Slight.

*Habit of flowering*.—Flowers on new growth, flowers are both terminal and axillary.
*Time of beginning of flowering*.—Mid-June through July, rebloom mid-August through October.
*Hardiness/cold tolerance*.—At least USDA Zone 5.

Stem:
*Number of stems per plant*.—7.
*Length of stem*.—150 cm.
*Diameter of stem*.—0.2 cm.
*Stem shape*.—Ribbed, gives appearance of striations.
*Stem strength*.—Strong and moderately flexible.
*Internode length*.—5.0 cm to 7.0 cm.
*Stem color*.—RHS 176A (Greyed Orange) sometimes furrowed; furrows RHS N172C (Greyed Orange).
*Stem texture and appearance*.—Medium coarse texture, slight pubescence and minute striations.

Foliage:
*Type*.—Mostly simple single leaves arranged opposite. Some lower leaves ternately compound; Lowest leaves on stems are sessile or almost sessile.
*Leaf length*.—Simple leaves 3.0 to 5.0 cm.
*Leaf width*.—Simple leaves 2.0 to 3.0 cm.
*Trifoliate leaf length*.—3.2 cm to 4.2 cm.
*Trifoliate leaf width*.—3.0 cm to 4.0 cm.
*Leaflet length*.—Trifoliate leaves 3.0 to 4.0 cm.
*Leaflet width*.—Trifoliate leaves 2.0 cm to 2.5 cm.
*Shape*.—Simple leaves elliptic, trifoliate leaflets obtuse.
*Apex*.—Broadly acuminate.
*Base*.—Simple leaves cordate, trifoliate leaves attenuate.
*Margin*.—Simple leaves wavy, few blunt teeth. Trifoliate leaves wavy.
*Lobing*.—Entire.
*Color*.—Upper surface of leaf: RHS 137A (Green). Lower leaf surface RHS 137C (Green).
*Variegation*.—Absent.
*Rugosity of upper surface of leaf*.—Mildly rugose.
*Rugosity of leaflet*.—Mildly rugose.
*Texture*.—Upper surface: Glaucous feel, slight slickness, pubescence absent. Lower surface: Sparsely pilose, faintly but distinctly reticulated.

Petiole:
*Length*.—4.0 cm.
*Diameter*.—0.1 cm.
*Texture*.—Sparsely long pubescent.
*Color*.—Top surface RHS 177A (Greyed Orange). Lower surface: RHS 138C (Green).

Petiolule:
*Attachment*.—Simple, petiolate. Trifoliate, sessile.
*Length*.—Sessile to 0.8 cm.
*Diameter*.—Sessile to 0.1 cm.
*Color*.—RHS 177A (Greyed Orange).
*Rachis*.—Absent.

Flowers: Erect, outward and upward facing. Two to several layers of sepals.
*Arrangement*.—Axillary and terminal.
*Flower bud*.—Shape: Conical. Length: 1.2 cm. Diameter: 1.0 cm. Color: RHS 145C (Yellow Green).
*Pedicel*.—Length of pedicel: 1.0 cm. Pedicel diameter: 0.15 cm. Pedicel color: RHS 136C (Green). Texture: Sparsely long pubescent.
*Average number of flowers per plant*.—130.
*Lastingness of the blooms*.—7-12 days weather dependent.
*Flower attitude*.—Erect, outward and upward facing.
*Flower type*.—Double.
*Flower diameter*.—6.5 cm to 7.2 cm.
*Flower depth*.—3.2 cm to 4.1 cm.
*Flower shape*.—Spreading double star.
*Flower cross-section, lateral view*.—Shallow saucer shape.
*Flower fragrance*.—Very lite to none.

Tepals:
*Quantity*.—9 to 12.
*Arrangement*.—Overlapping with multiple layers.
*Length*.—2.5 cm to 3.1 cm.
*Width*.—1.2 cm to 2.0 cm.
*Shape*.—Elliptic to ovate.
*Shape in cross-section*.—Wavy.
*Curvature in longitudinal section*.—Slight to none.
*Reflexing of apex*.—Slight to moderate.
*Apex*.—Obtuse.
*Base*.—Acute.
*Margin*.—Mostly entire with few wide spaced shallow indentations.
*Texture*.—Upper surface: Glabrous. Lower surface: Sparse finely pubescent.
*Number of colors of upper surface*.—3.
*Main color of upper surface*.—RHS 72C (Purple Pink).
*Secondary color of upper surface*.—RHS 71A (Purple Violet).
*Third tepal color*.—Upper surface: RHS 149D (Yellow green). Underside: RHS 149C (Yellow green).
*Distribution of secondary color of upper surface*.—Center third going just short of apex.
*Main color of lower surface*.—RHS 76A (Purple).
*Secondary color of lower surface*.—RHS 76D (Purple).
*Undulation of the margin*.—Moderate.
*Twisting along longitudinal axis*.—Slight.
*Petaloid staminodes*.—Absent.

Reproductive organs:
*Stamen*.—Number: 65 to 85. Filament length: 0.8 cm. Anther shape: Linear. Anther length: 0.3 cm. Filament color: RHS 160C (Greyed Yellow). Anther color: RHS 145D (Greyed Yellow).
*Pistil*.—Number: 25. Length: 0.5 cm. Stigma shape: Linear with a slight curve. Stigma color: RHS 145B (Yellow).
*Style*.—Length: 0.2 cm. Color: RHS 146A (Yellow Green).
*Ovary*.—Color: RHS 143D (Yellow Green).
*Pollen*.—None observed.

Fruit and seed set: No seed observed.

Disease and pest/insect resistance: No resistance has been noted.

COMPARISON WITH PARENTAL PLANT AND KNOWN VARIETY

'DP136' is a distinct variety of *Clematis* and is distinguished from it female parent as described in Table 1:

TABLE 1

| Comparison with the Female Parent | | |
|---|---|---|
| Trait | Variety 'DP136' | Female parent |
| Extra tepals on new growth | Consistently produces extra tepals | Single row of tepals |
| Margins of tepals | Ruffled margins | Wavy margins |

'DP136' is most similar to the commercial *Clematis* variety 'Floral Dance' (unpatented). Differences between the varieties are described in Table 2.

TABLE 2

| Comparison with Commercial Line | | |
|---|---|---|
| Trait | Variety 'DP136' | 'Floral Dance' |
| Remontant | Strongly remontant | Less remontant |
| Tepals | Ruffled margins | Smooth Margins |

I claim:

1. A new and distinct cultivar of *Clematis* plant named 'DP136' as illustrated and described herein.

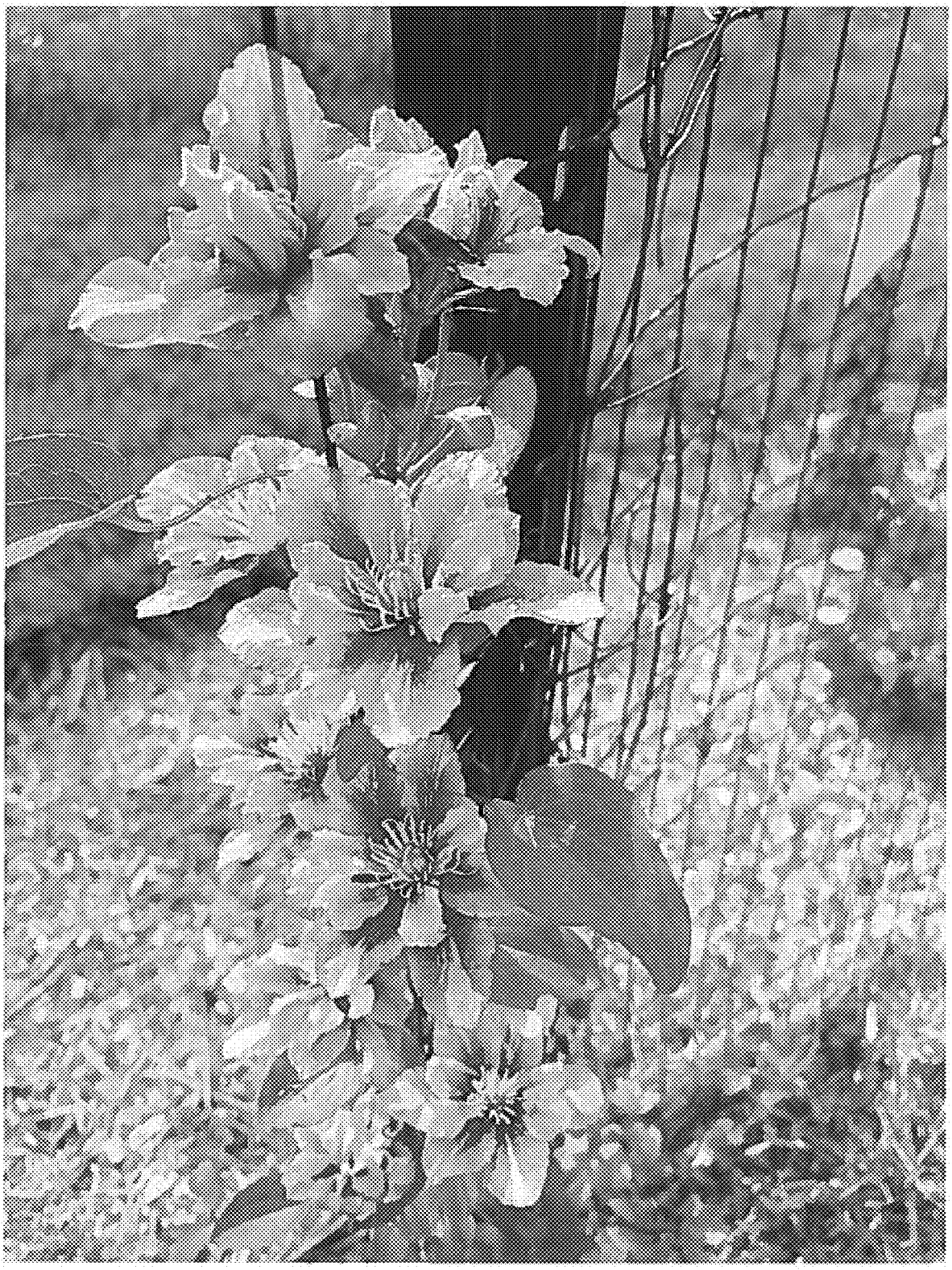

* * * * *